(12) United States Patent
Johnson

(10) Patent No.: US 6,293,795 B1
(45) Date of Patent: Sep. 25, 2001

(54) ROTARY HANDPIECE FOR ENDODONTIC INSTRUMENTATION

(75) Inventor: William B. Johnson, Tulsa, OK (US)

(73) Assignee: Dentsply Research & Development Corp.

(*) Notice: Subject to any disclaimer, the term of this patent is extended or adjusted under 35 U.S.C. 154(b) by 0 days.

(21) Appl. No.: 09/614,851

(22) Filed: Jul. 12, 2000

Related U.S. Application Data

(60) Provisional application No. 60/143,584, filed on Jul. 13, 1999.

(51) Int. Cl.[7] .................................................. A61C 1/07
(52) U.S. Cl. ............................................. 433/118; 433/102
(58) Field of Search ..................................... 433/118, 122, 433/120, 123, 124, 133, 131, 102

(56) References Cited

U.S. PATENT DOCUMENTS

| | | |
|---|---|---|
| 3,900,952 | 8/1975 | Landgraf et al. . |
| 4,007,529 | 2/1977 | Fleer . |
| 4,289,849 | 9/1981 | Lustig et al. ........................ 433/123 |
| 4,544,356 | 10/1985 | Gardella et al. ..................... 433/122 |
| 4,571,183 | 2/1986 | Nash ................................... 433/116 |
| 4,611,508 | 9/1986 | Roane ..................................... 76/24 |
| 4,629,426 | 12/1986 | Levy .................................... 433/118 |
| 4,773,855 | 9/1988 | Levy .................................... 433/102 |
| 4,834,653 | 5/1989 | Edwardson .......................... 433/118 |
| 4,911,639 | 3/1990 | Jacklich .............................. 433/102 |
| 5,017,134 | 5/1991 | Saito et al. ............................ 433/72 |
| 5,096,419 | 3/1992 | Kobayashi et al. .................... 433/72 |
| 5,538,423 | 7/1996 | Coss et al. ............................. 433/27 |
| 5,569,034 | 10/1996 | Meller et al. ....................... 433/105 |
| 5,586,886 | 12/1996 | Roane ................................. 433/224 |
| 5,639,236 | 6/1997 | Martin ................................. 433/131 |
| 5,902,105 | 5/1999 | Uejima et al. ......................... 433/27 |
| 5,938,441 | 8/1999 | Brenner .............................. 433/132 |
| 5,944,523 | 8/1999 | Badoz ................................. 433/131 |
| 5,975,900 | 11/1999 | Garman ............................... 433/105 |

FOREIGN PATENT DOCUMENTS

| | | |
|---|---|---|
| 195-09 840 | 3/1995 | (DE) . |
| 196 28 854 | 1/1997 | (DE) . |
| 0 118 992 | 2/1984 | (EP) . |
| 60-185544 | 9/1985 | (JP) . |

OTHER PUBLICATIONS

"Torsional Properties of the Canal Master Instrument"; Gary R. Massa et al., Journal of Endedentics vol. 18, No. 5, May 1992.

"An Evaluation of the Canal Master, Balanced–Force, and Step–Back Techniques". Philip J. Hankins et al., Journal of Endodontics, vol. 22, No. 3, Mar. 1996.

"Comparison of Root Canal Preparation Using Different Automated Devices and Hand Instrumentation"; Michael Hülsmann et al. Journal of Endodontics, vol. 19, No. 3, Mar. 1993.

"Histologic Evaluation of Three Endodontic Instrument/ Preparation Techniques"; M.L. Zuolo et al. ; University of Iowa College of Dentistry; Published Jan. 15, 1992.

"Histomorphometric Comparison of Canals Prepared by Four Techniques"; J. Craig Baumgartner et al.; Journal of Endodontics, vol. 18, No. 11, Nov. 1992.

*Primary Examiner*—Cary E. O'Connor
(74) *Attorney, Agent, or Firm*—James B. Bieber

(57) ABSTRACT

The invention is an endodontic handpiece, its control system and method of use for rotating an endodontic file to clean a root canal. The invention control system provides for rotating a file clockwise or counterclockwise through a desired first arc of rotation and, next, sequentially rotating the instrument in the opposite direction of the first arc of rotation through a second arc of rotation, wherein the first arc of rotation exceeds the second arc of rotation such that sequentially occurring rotations cause debris material removed in cleaning the canal to be ejected upwardly from the clean surfaces as such file is advanced in cleaning the canal.

6 Claims, 1 Drawing Sheet

ROTARY HANDPIECE FOR ENDODONTIC INSTRUMENTATION

This application claims benefit of Prov. No. 60/143,584, filed Jul. 13, 1999.

BACKGROUND OF THE INVENTION

1. Field of the Invention

The present invention relates to a handpiece for rotating endodontic files to clean and enlarge root canals of teeth. More particularly, the invention focuses upon a handpiece and its control system and method of use that improves debris removal while reducing risk of file breakage.

2. Description of the Prior Art

A key procedure in endodontic therapy of treating an infected tooth is cleaning and enlarging tooth root canals of the tooth prior to filling with an inert obturating material such as gutta percha. Such a procedure wherein infected tissues are successfully removed from the tooth greatly improves the likelihood that a patient will retain the tooth rather than need to have it extracted. The procedure for debridment and cleaning of infected material from the canal and to properly shape the canal to receive the obturating material is time consuming, generally employing a series of endodontic files that are rotated and advanced into the canal to clean canal surfaces and eject the debridment material from the canal for removal.

In the past, endodontic files were employed by the dentist manually, a very tedious process requiring substantial skill. It soon became evident that employing a handpiece to mechanically duplicate hand techniques, including rotating a file, would be a beneficial improvement in efficiency. However, a difficulty with motorized rotation or engine-driving of files is that the dentist sacrifices his "feel" and control of the procedure. The files are typically provided with helical cutting edges, presenting a danger of threading or screwing into the canal surfaces. Under such conditions a file, in negotiating tight curves or other root canal irregularities, might "lock up" and be subjected to excessive torque that could cause the file to fail by breaking. Additionally, rotation of instruments around a curve produces internal stresses resulting in metal fatigue that may cause a file to fail by breaking. Metal fatigue is induced more rapidly as the degree of curvature increases and/or the radius of the curve decreases. Such damaging results may require an extremely difficult effort at extraction of the broken file or other remedial action, including even extraction of the tooth. The dangers of lateral perforation, straightening, zipping and ledging are also all enhanced by engine-driven instrumentation.

Various rotary handpiece designs and techniques for using them have developed, some focused upon varying the motion of the files from simple rotation to reciprocating eliptical patterns, in the effort to duplicate hand operating procedures. Other handpiece improvements have focused upon controlling engine parameters, particularly by reducing speeds of rotation, setting limitations on torque applied to the file and the like to avoid file breakage.

An earlier limitation of the overall endodontic preparation process was lack of flexibility of files, which tended to discourage engine-driven procedures altogether, particularly with respect to aggressive K-files. New file designs, including for example radial landed cutting edges, that avoid screwing-in and which are made of highly flexible nickel-titanium alloys present new opportunities for engine-driven procedures. These files will better follow root canal curves, but even so may be at risk of metal fatigue as they rotate in curved canals. Of course, new files and procedures must insure that adequate removal of debris is achieved.

It is an objective of the present invention to provide a handpiece and control systems and method of use that operate at appropriate speed and torque, positively act to avoid imparting excessive torque to a file to cause a breakage, reduce the buildup of internal stress in the metal, improve tactile feedback and insure improved removal of debris while properly shaping the canal to receive obturating material.

SUMMARY OF THE INVENTION

The invention includes a rotary handpiece, related control systems, and a method of use for rotating an endodontic instrument or file in a manner that significantly reduces the possibility of lock-up or imparting excessive torque and internal stress to a file, yet continues removal of debris from the canal. A key feature of the invention is inclusion of a control system for an electric motor driving the handpiece file that rotates the file through a cutting or planing first arc of rotation, preferably clockwise, and sequentially rotates said file through a second arc of rotation, preferably counterclockwise, wherein the first arc of rotation exceeds that of the second arc of rotation such that material debrided from canal surfaces is ejected from the cleaned surfaces as the file is advanced in the canal.

In a preferred rotary handpiece of the invention, the first arc of rotation is about 90–180° (120°) and the counter, second arc of rotation is about 45–120° (90°).

DESCRIPTION OF THE PREFERRED EMBODIMENTS

Figure 1:
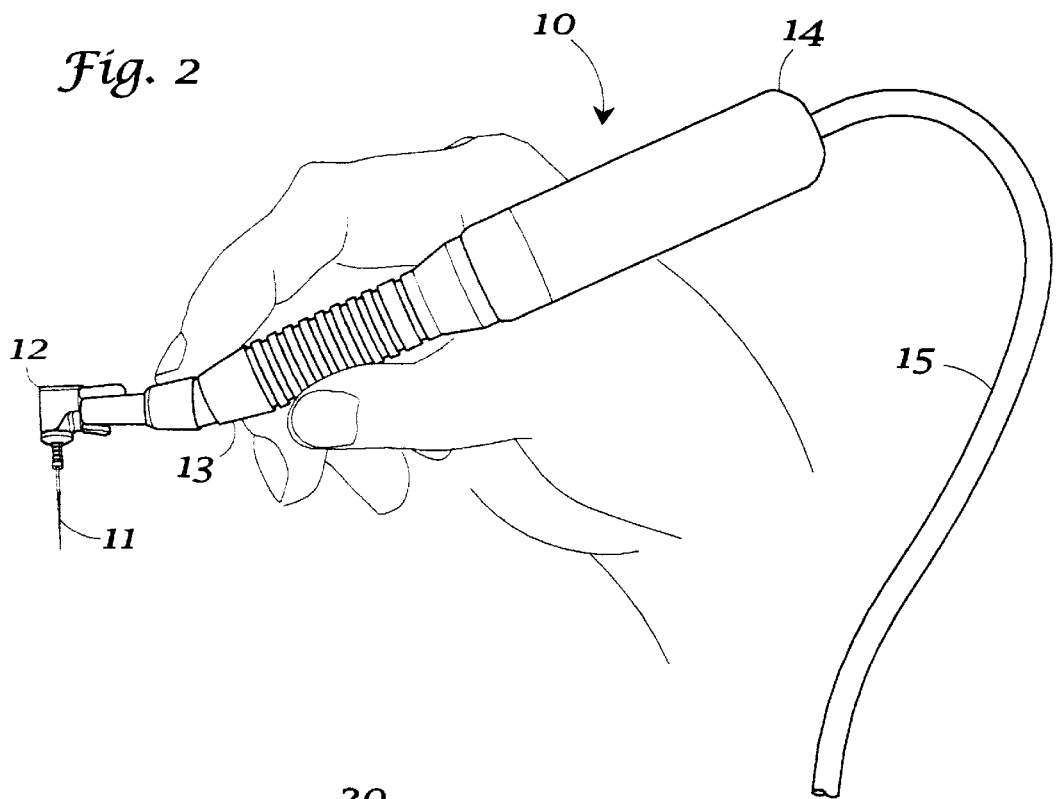
FIG. 1 is a schematic view of an embodiment of an endodontic handpiece of the invention and portions of its control system.
Figure 1:
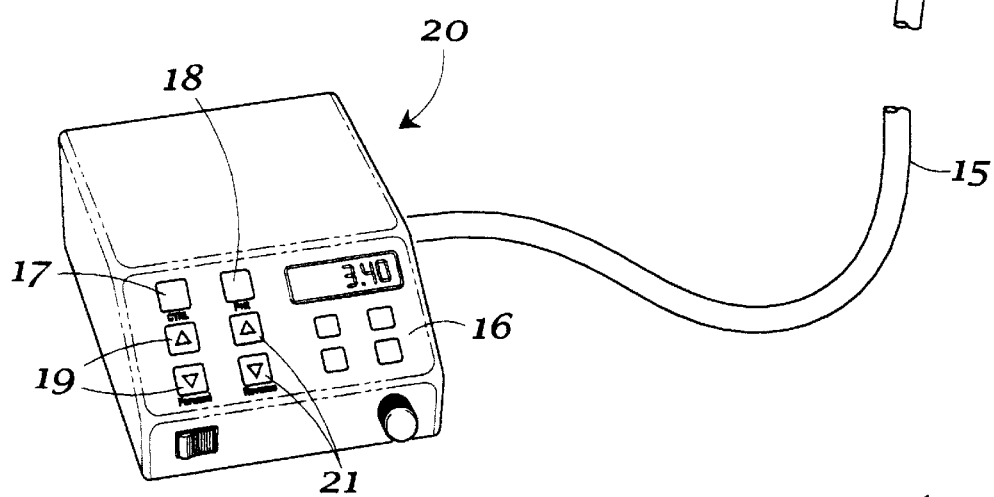

Referring to FIG. 1, a schematic representation of a preferred embodiment of the endodontic handpiece 10 and its control system 20 is shown. An endodontic instrument or file 11 is held securely in a chuck of a handpiece head 12 for rotation about its longitudinal axis. It is noted that any endodontic instrument of useful design may be employed. The head 12 is an integral component of a conventional contra angle, providing a drive train and gears (not shown in detail) necessary to rotate the file 11 at a desired rate of rotation, typically at a 16:1 reduction from a drive motor rate of rotation. An electric motor 14 is fastened to said contra angle 13, by for example complementary threaded body parts, engaging the contra angle drive train to rotate the file. The motor 14 is connected by a control cable 15 to the control system 20 microprocessor and keyboard 16 (shown schematically in part) which is capable of electronically controlling and input/output programming of desired values of motor parameters such as speed, torque, direction of rotation and the like, for a selected contra angle type and reduction capability and selected types of files. Such a motor and control system is the ATR Endojolly Tecnika Electrodontic Micromotor sold by ATR, SAS of Pistoia, Italy and described in ATR Users Manual, Report Number 99/45, incorporated herein by reference, which describes the hardware and software specifications and operation thereof The microprocessor 16, including software (not shown) provides means for setting the regime or method of rotation of the endodontic file 11, which method is a key element of the present invention. The ATR microprocessor keyboard 16 includes a control (CTRL) key 17 and a "forward and reverse" (F+R) key 18 to access setting forward rotation key 19 between 0.05 to 2.5 seconds and reverse rotation key 21 which settings appear in a display. In addition, the keyboard 16 provides similar keys (not shown) allowing setting of the time between the forward and reverse motions, from substantially instant to up to a 2.5 second delay.

The microprocessor also provides input keys (not shown) for setting a maximum amount of torque to be applied to a file, said limitation to avoid exceeding breaking stresses. The amount of maximum torque allowed is set with regard to the particular type of file employed, i.e. nickel titanium, for example.

In operation, when an operator programs a particular torque setting, the ATR microprocessor and motor will respond electronically if the file exceeds the limit by changing the file's direction of rotation. The system may be programmed, for example, to reverse for approximately 1–1½ revolutions, then automatically continue rotating in the clockwise forward direction. In a unique regime of the invention, the control system is programmed such that the file is rotated a desired number of degrees forward or clockwise and then automatically reverses to counterclockwise rotation for limited number of degrees. The preferred regime of operation is that the forward rotation exceeds that of the reverse rotation such that the file rotating through a series of forward and reverse motions, completes a circle of rotation such that cleaning of the root canal proceeds by means of a series of cutting and ejection of debris cycles.

In a preferred regime, the clockwise or forward rotation is set at between 90 and 180 degrees and the counterclockwise reverse arc of rotation, less than the first arc of rotation is set at about 45 to 120 degrees. Once the arcs of rotation are set, the endodontist having also set the other handpiece parameters for speed of rotation, torque and the like, the root canal cleaning proceeds to completion. For example, for a file rotating at 250 revolutions per minute with a desired first arc of rotation of about 120 degrees and a second arc of rotation of 90 degrees, the endodontist would input the forward time of rotation of 0.08 seconds and reverse rotation of 0.06 seconds, as well as a substantially instantaneous or other desired time between the forward and reverse motions.

Figure 2:
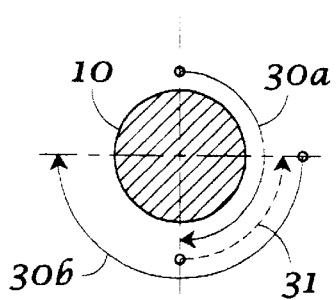
FIG. 2 is a schematic cross-sectional view of a file showing a preferred first and second arcs of rotation.

Another preferred regime of operation is shown in FIG. 2, which shows schematically a file 11 in cross-section being rotated through one reverse cycle of motion. The first forward rotation 30a is 180 degrees, followed by the reverse arc of rotation 31 of 90 degrees, followed by the second arc of forward rotation 30b of 180 degrees, which cycles continue with the file being advanced in the canal.

Having described the preferred embodiment of the invention with references to the accompanied drawings, it is to be understood that the invention is not limited to that precise embodiment and at various changes and modifications may be affected therein by one skilled in the art without departing from the scope or spirit of the invention as defined in the dependant claims we claim.

What is claimed:

1. A rotary handpiece for cleaning and enlarging a root canal of a tooth, said handpiece providing rotation to an endodontic instrument secured in said handpiece, comprising:

a chuck that secures said endodontic instrument to said handpiece for rotation about its longitudinal axis;

an electric motor that rotates said instrument;

a control system for said motor having input and output means to control rotation of said instrument, said control system
      rotating said instrument clockwise or counter-clockwise, through a first arc of rotation and, next sequentially,
      rotating said instrument in the opposite direction of the first arc of rotation through a second arc of rotation, wherein said first arc of rotation exceeds said second arc of rotation such that said sequentially occurring rotations cause debris material removed in cleaning said canal to be ejected upwardly from said cleaned canal surfaces as such file is advanced in cleaning said canal.

2. The rotary handpiece of claim 1 wherein said clockwise first arc of rotation is at least about 90–180° and said second arc of rotation is at least about 45–120°.

3. The rotary handpiece of claim 2 wherein said first arc of rotation is about 120° of arc and said second arc of rotation is about 90° of arc.

4. The rotary handpiece of claim 1 wherein said handpiece driving system further includes a torque sensor that initiates reversal of initial direction of rotation only when a set point has been exceeded.

5. A method of cleaning and enlarging a root canal of a tooth, comprising:

(a) rotating an endodontic instrument with a handpiece having a sensor and control for selectively detecting and limiting torque and rotation applied to said instrument;

(b) advancing said rotating instrument in said root canal wherein canal surfaces are substantially cleaned and resulting debris ejected therefrom until said canal is cleaned or a selected torque limit is exceeded;

(c) reversing, at said selected torque limit, the direction of rotation of said instrument, initiating a sequence wherein said instrument is rotating through a first arc of rotation, reversing direction of rotation, said instrument then rotating in the opposite rotational direction of said first arc through a second arc of rotation, said rotations occurring sequentially wherein said first arc of rotation exceeds said second arc of rotation; and, (d) advancing said sequentially rotating instrument into said root canal to a desired depth whereby canal surfaces are substantially cleaned of debris which is ejected from said canal.

6. The method of claim 5 wherein said first arc of rotation is at least about 120° and said second arc of rotation is at least about 90°.

* * * * *